United States Patent
Nair et al.

(10) Patent No.: US 11,596,384 B2
(45) Date of Patent: Mar. 7, 2023

(54) INTRALUMINAL ULTRASOUND VESSEL BORDER SELECTION AND ASSOCIATED DEVICES, SYSTEMS, AND METHODS

(71) Applicant: VOLCANO CORPORATION, San Diego, CA (US)

(72) Inventors: Anuja Nair, San Diego, CA (US); Rebecca Ann Jenkins, San Diego, CA (US)

(73) Assignee: PHILIPS IMAGE GUIDED THERAPY CORPORATION, San Diego, CA (US)

(*) Notice: Subject to any disclaimer, the term of this patent is extended or adjusted under 35 U.S.C. 154(b) by 470 days.

(21) Appl. No.: 16/661,360

(22) Filed: Oct. 23, 2019

(65) Prior Publication Data

US 2020/0129147 A1   Apr. 30, 2020

Related U.S. Application Data

(60) Provisional application No. 62/750,996, filed on Oct. 26, 2018.

(51) Int. Cl.
*A61B 8/00* (2006.01)
*A61B 8/12* (2006.01)
(Continued)

(52) U.S. Cl.
CPC ............... *A61B 8/12* (2013.01); *A61B 8/085* (2013.01); *G06N 20/00* (2019.01); *G06T 7/0012* (2013.01);
(Continued)

(58) Field of Classification Search
CPC ......... A61B 8/12; A61B 8/085; A61B 8/0891; A61B 8/461; A61B 8/463; A61B 8/469; G06N 20/00; G06N 3/0454; G06T 7/0012; G06T 7/149; G06T 2207/10132; G06T 2207/30101; G06T 2207/20081; G06T 2207/20084; G06T 2207/20096;
(Continued)

(56) References Cited

U.S. PATENT DOCUMENTS 6,200,268 B1   3/2001   Vince
6,381,350 B1   4/2002   Klingensmith
(Continued)

FOREIGN PATENT DOCUMENTS

WO   2019175004 A1   9/2019

*Primary Examiner* — Joel Lamprecht

(57) ABSTRACT

Disclosed is an intraluminal ultrasound imaging system, including a processor circuit in communication with an intraluminal ultrasound imaging catheter, wherein the processor circuit is configured to receive a plurality of intraluminal ultrasound images obtained by the intraluminal ultrasound imaging catheter during movement of the intraluminal ultrasound imaging catheter within a body lumen of a patient. The processor circuit is further configured to select an image from among the plurality of intraluminal ultrasound images, generate at least two border contours associated with the lumen within the selected image, display the border contours associated with the lumen, each overlaid on a separate instance of the selected image, receive a user input selecting one of the border contours; and display the selected image overlaid with the selected border contour.

22 Claims, 9 Drawing Sheets

(51) Int. Cl.
   *G06T 7/149* (2017.01)
   *G06N 20/00* (2019.01)
   *A61B 8/08* (2006.01)
   *G06T 7/00* (2017.01)

(52) U.S. Cl.
   CPC .... *G06T 7/149* (2017.01); *G06T 2207/10132* (2013.01); *G06T 2207/30101* (2013.01)

(58) Field of Classification Search
   CPC ........... G06T 7/12; G06T 7/174; G16H 30/40; G16H 40/63
   See application file for complete search history.

(56) References Cited

U.S. PATENT DOCUMENTS

| | | |
|---|---|---|
| 7,074,188 B2 | 7/2006 | Nair |
| 7,175,597 B2 | 2/2007 | Vince |
| 7,215,802 B2 | 5/2007 | Klingensmith |
| 7,359,554 B2 | 4/2008 | Klingensmith |
| 7,463,759 B2 | 12/2008 | Klingensmith |
| 7,846,101 B2 | 12/2010 | Eberle |
| 11,272,845 B2 * | 3/2022 | Cheline ................ A61B 5/0086 |
| 2004/0197015 A1 | 10/2004 | Fan |
| 2007/0036404 A1 | 2/2007 | Li |
| 2013/0216114 A1 * | 8/2013 | Courtney ................ A61B 6/03 382/128 |
| 2014/0050304 A1 | 2/2014 | Florent |
| 2019/0095738 A1 | 3/2019 | Sharma |
| 2019/0282199 A1 | 9/2019 | Merritt |

\* cited by examiner

INTRALUMINAL ULTRASOUND VESSEL BORDER SELECTION AND ASSOCIATED DEVICES, SYSTEMS, AND METHODS

CROSS REFERENCE TO RELATED APPLICATIONS

This application claims priority to and the benefit of U.S. Provisional Patent Application No. 62/750,996, filed Oct. 26, 2018, which is incorporated by reference herein in its entirety.

TECHNICAL FIELD

The subject matter described herein relates to a system for medical imaging. In particular, the disclosed system provides a system for identifying and selecting automatically detected lumen and/or vessel boundaries. This system has particular but not exclusive utility for diagnosis and treatment of vascular diseases.

BACKGROUND

Intravascular ultrasound (IVUS) is used in both coronary vascular procedures and peripheral vascular procedures, such as angioplasty and stenting, IVC-filter retrieval, EVAR and FEVAR (and similar on the abdominal trait) atherectomy and thrombectomy. Different diseases or medical procedures produce physical features with different size, structure, density, water content, and accessibility for imaging sensors. For example, a deep-vein thrombosis (DVT) produces a clot of blood cells, whereas post-thrombotic syndrome (PTS) produces webbing (synechiae) or other residual structural effects in a vessel that have scar-tissue-like composition or similar composition to the vessel wall itself, and may thus be difficult to distinguish from the vessel wall. A stent is a dense (e.g., metallic) object that may be placed in a vessel or lumen to hold the vessel or lumen open to a particular diameter. A compression occurs when anatomical structures outside the vessel or lumen impinge on the vessel or lumen, constricting it.

In some cases, intraluminal medical imaging is carried out with an IVUS device including one or more ultrasound transducers. The IVUS device may be passed into the vessel and guided to the area to be imaged. The transducers emit ultrasonic energy and receive ultrasound echoes reflected from the vessel. The ultrasound echoes are processed to create an image or plurality of images of the vessel of interest. The image of the vessel of interest may include one or more lesions or blockages in the vessel. A stent may be placed within the vessel to treat these blockages and intraluminal imaging may be carried out to view the placement of the stent within the vessel. Other types of treatment include thrombectomy, ablation, angioplasty, pharmaceuticals, etc.

Automated algorithms can provide users of intravascular imaging systems with real-time measurements (e.g., diameter or cross-sectional area of a vessel wall or vessel lumen) that are relevant for clinical image interpretation. While the goal of such algorithms is to be as accurate as possible with the automated measurements, these algorithms do not always identify the same boundaries or measurements that a human would, particularly around ambiguous areas such as vessel side branches. As a result, alteration of an identified border or measurement is often necessary. In those cases where the algorithm results might need to be adjusted, or when a user wants to alter or edit the results, the typical means to do that is via some form of manual editing, which can be difficult or time-consuming and may also be subject to error. Hence, there is a need for improved systems and methods that permit streamlined correction of an identified border, and any calculations derived therefrom.

The information included in this Background section of the specification, including any references cited herein and any description or discussion thereof, is included for technical reference purposes only and is not to be regarded as subject matter by which the scope of the disclosure is to be bound.

SUMMARY

Disclosed is a system for advantageously enabling easy editing of measurements and borders during use of IVUS, or any other imaging modality from which vessel borders can be identified. An automated algorithm accomplishes this by providing a user with two, three, four, or more automatically identified vessel border options to quickly select from, ranked in order of computed probability. These options may be presented simultaneously to the user. This may for example be done visually (e.g., by showing three different instances of the same IVUS image with three different border options) and/or numerically (e.g., by presenting three different numerical values associated with the three different vessel border contours). This reduces the amount of time required to edit measurements, by avoiding the need for users to draw their measurement corrections manually. Such automated algorithms can be based on classical techniques or may employ machine learning or deep learning techniques, or other types of artificial intelligence, or combinations thereof. The system is hereinafter referred to as a vessel border selection system.

An algorithm, based on probability, presents the user with 2, 3 or more options to choose from quickly, instead of having to make manual edits to an automatically identified vessel border. This concept can be implemented for intravascular imaging (e.g., intravascular ultrasound or IVUS), but can also be applied to other clinical imaging modalities (OCT, external, ultrasound, x-ray, angiograms or venograms, CT, MRI, etc.). The system can also provide the user with the ability to edit a selected contour manually.

The vessel border selection system disclosed herein has particular, but not exclusive, utility for intraluminal ultrasound imaging procedures. One general aspect of the vessel border selection system includes an intraluminal ultrasound imaging system, including: a processor circuit configured for communication with an intraluminal ultrasound imaging catheter, where the processor circuit is configured to: receive a plurality of intraluminal ultrasound images obtained by the intraluminal ultrasound imaging catheter during movement of the intraluminal ultrasound imaging catheter within a body lumen of a patient; select an image from among the plurality of intraluminal ultrasound images; generate at least two border contours associated with the lumen within the selected image; output, to a display in communication with the processor circuit, a screen display including the at least two border contours associated with the lumen, each overlaid on a separate instance of the selected image; receive, from a user interface in communication with the processor circuit, a first user input selecting one of the border contours; and output, to the display, the selected image overlaid with the selected border contour. Other embodiments of this aspect include corresponding computer systems, apparatus, and computer programs recorded on one or more computer storage devices, each configured to perform the actions of the methods.

Implementations may include one or more of the following features. The system where the processor circuit is further configured to: generate a derived border contour associated with the lumen for at least one additional image from the plurality of intraluminal ultrasound images by propagating the selected border contour of the selected image to the at least one additional image. The system where the processor circuit is further configured to: generate a geometric measurement for each border contour; and output, to the display, the geometric measurement for each border contour. The system where the geometric measurement includes at least one of a lumen diameter, a vessel wall outer diameter, a lumen cross-sectional area, or a vessel cross-sectional area. The system where the processor circuit is further configured to: receive, from the user interface, a second user input to edit the selected border contour; recalculate the geometric measurement based on the edited border contour; and output, to the display, the selected image overlaid with the edited border contour, along with the recalculated geometric measurement. The system where the processor circuit is configured to generate the at least two border contours based on a first value of a statistical measure, and where the processor circuit is configured to generate a different border contour based on a second value of the statistical measure. The system where the processor circuit is configured to receive a second input, from the user interface, to change the statistical measure from the first value to the second value. The system where the processor circuit is configured to generate the at least two border contours based on a machine learning algorithm. The system further including: the intraluminal ultrasound imaging catheter. The system further including: the display; and the user interface, where the user interface includes a touch screen of the display. Implementations of the described techniques may include hardware, a method or process, or computer software on a computer-accessible medium.

One general aspect includes an intraluminal ultrasound imaging method, including: receiving, at a processor circuit in communication with an intraluminal ultrasound imaging catheter, a plurality of intraluminal ultrasound images obtained by the intraluminal ultrasound imaging catheter during movement of the intraluminal ultrasound imaging catheter within a body lumen of a patient; selecting, using the processor circuit, an image from among the plurality of intraluminal ultrasound images; generating, using the processor circuit, at least two border contours associated with the lumen within the selected image; outputting, to a display in communication with the processor circuit, a screen display including the at least two border contours associated with the lumen, each overlaid on a separate instance of the selected image; receiving, from a user interface in communication with the processor circuit, a first user input selecting one of the border contours; and outputting to the display, using the processor circuit, the selected image overlaid with the selected border contour. Other embodiments of this aspect include corresponding computer systems, apparatus, and computer programs recorded on one or more computer storage devices, each configured to perform the actions of the methods.

Implementations may include one or more of the following features. The method further including: generating a derived border contour associated with the lumen for at least one additional image from the plurality of intraluminal ultrasound images by propagating the selected border contour of the selected image to the at least one additional image. The method further including: generating a geometric measurement for each border contour; and outputting to the display the geometric measurement for each border contour. The method where the geometric measurement includes at least one of a lumen diameter, a vessel wall outer diameter, a lumen cross-sectional area, or a vessel cross-sectional area. The method further including: receiving, from the user interface, a second user input to edit the selected border contour; recalculating the geometric measurement based on the edited border contour; and outputting, to the display, the selected image overlaid with the edited border contour, along with the recalculated geometric measurement. The method further including: generating the at least two border contours based on a first value of a statistical measure; and generating a different border contour based on a second value of the statistical measure. The method further including receiving a second input, from the user interface, to change the statistical measure from the first value to the second value. The method where the at least two border contours are generated based on a machine learning algorithm. Implementations of the described techniques may include hardware, a method or process, or computer software on a computer-accessible medium.

One general aspect includes an intravascular ultrasound imaging system for use in peripheral blood vessels, the system including: an intravascular ultrasound imaging catheter configured to obtain a plurality of intravascular ultrasound images during movement of the intravascular ultrasound imaging catheter within a peripheral blood vessel of a patient; and a processor circuit configured for communication with the intravascular ultrasound imaging catheter, where the processor circuit is configured to: receive the plurality of intravascular ultrasound images obtained by the intravascular ultrasound imaging catheter; select an image from among the plurality of intravascular ultrasound images; generate at least two border contours associated with the peripheral blood vessel within the selected image; output, to a display in communication with the processor circuit, a screen display including the at least two border contours associated with the peripheral blood vessel, each overlaid on a separate instance of the selected image; receive, from a user interface in communication with the processor circuit, a first user input selecting one of the border contours; and output, to the display, the selected image overlaid with the selected border contour. Other embodiments of this aspect include corresponding computer systems, apparatus, and computer programs recorded on one or more computer storage devices, each configured to perform the actions of the methods.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the vessel border selection system, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which.

DETAILED DESCRIPTION

Figure 1:
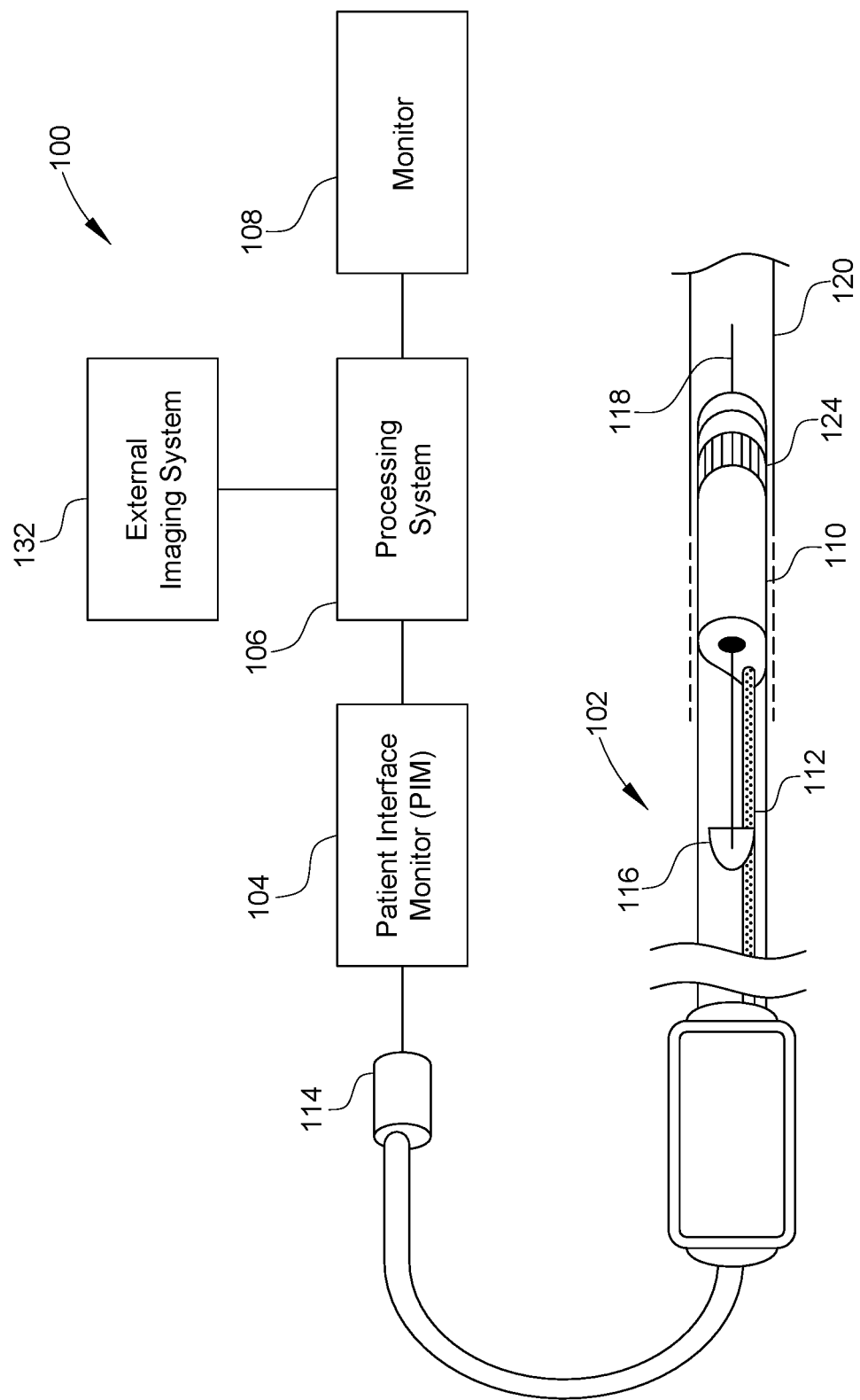
FIG. 1 is a diagrammatic schematic view of an intraluminal imaging system, according to aspects of the present disclosure.

The present disclosure relates generally to medical imaging, including imaging associated with a body lumen of a patient using an intraluminal imaging device. For example, the present disclosure describes systems, devices, and methods for identification and measurement of the borders of a vessel or other organ, during use of intravascular ultrasound (IVUS) and other imaging modalities, by providing the user with two, three, or more automatically generated border options to select from, ranked in order based on algorithmically determined probabilities. Current methods of editing a vessel or organ border involve manual interaction by a user to either re-draw or by some means redirect the features that an automated algorithm has determined on an image. Such editing techniques can be time-consuming and also difficult or error-prone for some users. The present disclosure reduces the amount of time required for a clinician or other user to edit vessel or organ border contours, and the measurements derived therefrom, by avoiding the requirement for the user to draw their corrections to a border or boundary manually. One advantage of the present disclosure is that with easy one-click selection between multiple possible contours, the process is made much easier and much less time-consuming for the user. In some embodiments, manual editing may still be available as a fallback option, if none of the automatically computed boundary contours matches with the expectation or desire of the clinician or other user. This concept can be implemented for intravascular imaging (IVUS), and also with other clinical imaging modalities (angiograms or venograms, CT, etc.). As long as there is an automated algorithm associated with finding some feature or features within the images, there exists a need to edit those findings, and thus a need to streamline the editing process.

The present disclosure offers numerous advantages, including easy and fast editing of automatically detected features, based on easy selection from among multiple, automatically detected options, ranked by probabilities calculated from the automated algorithm. With machine learning/deep learning or classical algorithms there are means to determine the probability of the features an algorithm is built to detect. For example, in an intravascular ultrasound image (IVUS) one might try to segment the lesion by detecting the blood-lumen border and the outer artery or vein wall border. By calculating the probability of the automated border detection, 2 or 3 or more options can be calculated that are near in probability or other parameter(s) to the border that was calculated. Hence, when the user interacts with the system to edit a border, these options can be presented to the user to quickly pick the one closest to the border they would have manually drawn or corrected. This system is hereinafter referred to as a vessel border selection system.

The devices, systems, and methods described herein can include one or more features described in U.S. Provisional App. No. 62/750,983, filed 26 Oct. 2018, U.S. Provisional App. No. 62/751,268, filed 26 Oct. 2018, U.S. Provisional App. No. 62/751,289, filed 26 Oct. 2018, U.S. Provisional App. No. 62/750,996, filed 26 Oct. 2018, U.S. Provisional App. No. 62/751,167, filed 26 Oct. 2018, and U.S. Provisional App. No. 62/751,185, filed 26 Oct. 2018, each of which is hereby incorporated by reference in its entirety as though fully set forth herein.

The devices, systems, and methods described herein can also include one or more features described in U.S. Provisional App. No. 62/642,847, filed Mar. 14, 2018 (and a Non-Provisional application filed therefrom on Mar. 12, 2019 as U.S. Ser. No. 16/351,175), U.S. Provisional App. No. 62/712,009, filed Jul. 30, 2018, U.S. Provisional App. No. 62/711,927, filed Jul. 30, 2018, and U.S. Provisional App. No. 62/643,366, filed Mar. 15, 2018 (and a Non-Provisional application filed therefrom on Mar. 15, 2019 as U.S. Ser. No. 16/354,970), each of which is hereby incorporated by reference in its entirety as though fully set forth herein.

The present disclosure substantially aids a clinician in making sense of large volumes of intraluminal imaging data, and in reporting and treatment planning. The present disclosure accomplishes this by providing a quick, seamless process for identification, selection, and editing of the boundaries of a vessel or other organ, along with associated measurements. Implemented on a medical imaging console (e.g., an IVUS imaging console) in communication with a medical imaging sensor (e.g., an intraluminal ultrasound sensor), the vessel border selection system disclosed herein provides both time savings and an improvement in the accuracy of vessel border identification and measurement. This improved imaging workflow transforms a time-consuming process of manual marking, editing, and correction into a streamlined process involving both fewer steps and simpler steps. This occurs for example without the normally routine need for a clinician to draw a border contour over an image, or edit (e.g., drag and drop) the points that define the border contour. This unconventional approach improves the functioning of the medical imaging console and sensor, by automating vessel border identification and calculation steps that are normally performed manually by the clinician or other users.

The vessel border selection system may be implemented as a set of logical branches and mathematical operations, whose outputs are viewable on a display, and operated by a control process executing on a processor that accepts user inputs (e.g., from a user interface such as a keyboard, mouse, or touchscreen interface), and that is in communication with one or more medical imaging sensors (e.g., intraluminal ultrasound sensors). In that regard, the control process performs certain specific operations in response to different inputs or selections made by a user at the start of an imaging procedure, and may also respond to inputs made by the user during the procedure. Certain structures, functions, and operations of the processor, display, sensors, and user input systems are known in the art, while others are recited herein to enable novel features or aspects of the present disclosure with particularity.

Various types of intraluminal imaging systems are used in diagnosing and treating diseases. For example, intravascular ultrasound (IVUS) imaging is used as a diagnostic tool for visualizing vessels within a body of a patient. This may aid in assessing diseased or compressed vessels, such as arteries or veins, within the human body to determine the need for treatment, to optimize treatment, and/or to assess a treatment's effectiveness (e.g., through imaging of the vessel before and after treatment).

In some cases, intraluminal imaging is carried out with an IVUS device including one or more ultrasound transducers. The IVUS device may be passed into the vessel and guided to the area to be imaged. The transducers emit ultrasonic energy and receive ultrasound echoes reflected from the vessel. The ultrasound echoes are processed to create an image of the vessel of interest. The image of the vessel of interest may include one or more lesions or blockages in the vessel. A stent may be placed within the vessel to treat these blockages and intraluminal imaging may be carried out to view the placement of the stent within the vessel. Other types of treatment include thrombectomy, ablation, angioplasty, pharmaceuticals, etc.

The vessel border selection system eases the workload on the clinician, and permits certain aspects of vessel border identification, editing, and associated measurements to happen automatically, either during the IVUS procedure itself or during a review mode after the procedure, or combinations thereof.

These descriptions are provided for exemplary purposes only, and should not be considered to limit the scope of the vessel border selection system. Certain features may be added, removed, or modified without departing from the spirit of the claimed subject matter.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal imaging system incorporating the vessel border selection system, according to aspects of the present disclosure. The intraluminal imaging system 100 can be an intravascular ultrasound (IVUS) imaging system in some embodiments. The intraluminal imaging system 100 may include an intraluminal device 102, a patient interface module (PIM) 104, a console or processing system 106, a monitor 108, and an external imaging system 132 which may include angiography, ultrasound, X-ray, computed tomography (CT), magnetic resonance imaging (MRI), or other imaging technologies, equipment, and methods. The intraluminal device 102 is sized and shaped, and/or otherwise structurally arranged to be positioned within a body lumen of a patient. For example, the intraluminal device 102 can be a catheter, guide wire, guide catheter, pressure wire, and/or flow wire in various embodiments. In some circumstances, the system 100 may include additional elements and/or may be implemented without one or more of the elements illustrated in FIG. 1. For example, the system 100 may omit the external imaging system 132.

The intraluminal imaging system 100 (or intravascular imaging system) can be any type of imaging system suitable for use in the lumens or vasculature of a patient. In some embodiments, the intraluminal imaging system 100 is an intraluminal ultrasound (IVUS) imaging system. In other embodiments, the intraluminal imaging system 100 may include systems configured for forward looking intraluminal ultrasound (FL-IVUS) imaging, intraluminal photoacoustic (IVPA) imaging, intracardiac echocardiography (ICE), transesophageal echocardiography (TEE), and/or other suitable imaging modalities.

It is understood that the system 100 and/or device 102 can be configured to obtain any suitable intraluminal imaging data. In some embodiments, the device 102 may include an imaging component of any suitable imaging modality, such as optical imaging, optical coherence tomography (OCT), etc. In some embodiments, the device 102 may include any suitable non-imaging component, including a pressure sensor, a flow sensor, a temperature sensor, an optical fiber, a reflector, a mirror, a prism, an ablation element, a radio frequency (RF) electrode, a conductor, or combinations thereof. Generally, the device 102 can include an imaging element to obtain intraluminal imaging data associated with the lumen 120. The device 102 may be sized and shaped (and/or configured) for insertion into a vessel or lumen 120 of the patient.

The system 100 may be deployed in a catheterization laboratory having a control room. The processing system 106 may be located in the control room. Optionally, the processing system 106 may be located elsewhere, such as in the catheterization laboratory itself. The catheterization laboratory may include a sterile field while its associated control room may or may not be sterile depending on the procedure to be performed and/or on the health care facility. The catheterization laboratory and control room may be used to perform any number of medical imaging procedures such as angiography, fluoroscopy, CT, IVUS, virtual histology (VH), forward looking IVUS (FL-IVUS), intraluminal photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intraluminal palpography, transesophageal ultrasound, fluoroscopy, and other medical imaging modalities, or combinations thereof. In some embodiments, device 102 may be controlled from a remote location such as the control room, such than an operator is not required to be in close proximity to the patient.

The intraluminal device 102, PIM 104, monitor 108, and external imaging system 132 may be communicatively coupled directly or indirectly to the processing system 106. These elements may be communicatively coupled to the medical processing system 106 via a wired connection such as a standard copper link or a fiber optic link and/or via wireless connections using IEEE 802.11 Wi-Fi standards, Ultra Wide-Band (UWB) standards, wireless FireWire, wireless USB, or another high-speed wireless networking standard. The processing system 106 may be communicatively coupled to one or more data networks, e.g., a TCP/IP-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System (HIS) via a network connection.

At a high level, an ultrasound imaging intraluminal device 102 emits ultrasonic energy from a transducer array 124 included in scanner assembly 110 mounted near a distal end of the intraluminal device 102. The ultrasonic energy is reflected by tissue structures in the medium (such as a lumen 120) surrounding the scanner assembly 110, and the ultrasound echo signals are received by the transducer array 124. The scanner assembly 110 generates electrical signal(s) representative of the ultrasound echoes. The scanner assembly 110 can include one or more single ultrasound transducers and/or a transducer array 124 in any suitable configuration, such as a planar array, a curved array, a circumferential array, an annular array, etc. For example, the scanner assembly 110 can be a one-dimensional array or a two-dimensional array in some instances. In some instances, the scanner assembly 110 can be a rotational ultrasound device. The active area of the scanner assembly 110 can include one or more transducer materials and/or one or more segments of ultrasound elements (e.g., one or more rows, one or more columns, and/or one or more orientations) that can be uniformly or independently controlled and activated. The active area of the scanner assembly 110 can be patterned or structured in various basic or complex geometries. The scanner assembly 110 can be disposed in a side-looking orientation (e.g., ultrasonic energy emitted perpendicular and/or orthogonal to the longitudinal axis of the intraluminal device 102) and/or a forward-looking looking orientation (e.g., ultrasonic energy emitted parallel to and/or along the longitudinal axis). In some instances, the scanner assembly 110 is structurally arranged to emit and/or receive ultrasonic energy at an oblique angle relative to the longitudinal axis, in a proximal or distal direction. In some embodiments, ultrasonic energy emission can be electronically steered by selective triggering of one or more transducer elements of the scanner assembly 110.

The ultrasound transducer(s) of the scanner assembly 110 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In an embodiment the ultrasound transducer array 124 can include any suitable number of individual transducer elements or acoustic elements between 1 acoustic element and 1000 acoustic elements, including values such as 2 acoustic elements, 4 acoustic elements, 36 acoustic elements, 64 acoustic elements, 128 acoustic elements, 500 acoustic elements, 812 acoustic elements, and/or other values both larger and smaller.

The PIM 104 transfers the received echo signals to the processing system 106 where the ultrasound image (including the flow information) is reconstructed and displayed on the monitor 108. The console or processing system 106 can include a processor and a memory. The processing system 106 may be operable to facilitate the features of the intraluminal imaging system 100 described herein. For example, the processor can execute computer readable instructions stored on the non-transitory tangible computer readable medium.

The PIM 104 facilitates communication of signals between the processing system 106 and the scanner assembly 110 included in the intraluminal device 102. This communication may include providing commands to integrated circuit controller chip(s) within the intraluminal device 102, selecting particular element(s) on the transducer array 124 to be used for transmit and receive, providing the transmit trigger signals to the integrated circuit controller chip(s) to activate the transmitter circuitry to generate an electrical pulse to excite the selected transducer array element(s), and/or accepting amplified echo signals received from the selected transducer array element(s) via amplifiers included on the integrated circuit controller chip(s). In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the intraluminal device 102 including circuitry within the scanner assembly 110.

The processing system 106 receives echo data from the scanner assembly 110 by way of the PIM 104 and processes the data to reconstruct an image of the tissue structures in the medium surrounding the scanner assembly 110. Generally, the device 102 can be utilized within any suitable anatomy and/or body lumen of the patient. The processing system 106 outputs image data such that an image of the vessel or lumen 120, such as a cross-sectional IVUS image of the lumen 120, is displayed on the monitor 108. Lumen 120 may represent fluid filled or fluid-surrounded structures, both natural and man-made. Lumen 120 may be within a body of a patient. Lumen 120 may be a blood vessel, such as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

The controller or processing system 106 may include a processing circuit having one or more processors in communication with memory and/or other suitable tangible computer readable storage media. The controller or processing system 106 may be configured to carry out one or more aspects of the present disclosure. In some embodiments, the processing system 106 and the monitor 108 are separate components. In other embodiments, the processing system 106 and the monitor 108 are integrated in a single component. For example, the system 100 can include a touch screen device, including a housing having a touch screen display and a processor. The system 100 can include any suitable input device, such as a touch sensitive pad or touch screen display, keyboard/mouse, joystick, button, etc., for a user to select options shown on the monitor 108. The processing system 106, the monitor 108, the input device, and/or combinations thereof can be referenced as a controller of the system 100. The controller can be in communication with the device 102, the PIM 104, the processing system 106, the monitor 108, the input device, and/or other components of the system 100.

In some embodiments, the intraluminal device 102 includes some features similar to traditional solid-state IVUS catheters, such as the EagleEye® catheter available from Volcano Corporation and those disclosed in U.S. Pat. No. 7,846,101 hereby incorporated by reference in its entirety. For example, the intraluminal device 102 may include the scanner assembly 110 near a distal end of the intraluminal device 102 and a transmission line bundle 112 extending along the longitudinal body of the intraluminal device 102. The cable or transmission line bundle 112 can include a plurality of conductors, including one, two, three, four, five, six, seven, or more conductors.

The transmission line bundle 112 terminates in a PIM connector 114 at a proximal end of the intraluminal device 102. The PIM connector 114 electrically couples the transmission line bundle 112 to the PIM 104 and physically couples the intraluminal device 102 to the PIM 104. In an embodiment, the intraluminal device 102 further includes a guidewire exit port 116. Accordingly, in some instances the intraluminal device 102 is a rapid-exchange catheter. The guidewire exit port 116 allows a guidewire 118 to be inserted towards the distal end in order to direct the intraluminal device 102 through the lumen 120.

The monitor 108 may be a display device such as a computer monitor or other type of screen. The monitor 108 may be used to display selectable prompts, instructions, and visualizations of imaging data to a user. In some embodiments, the monitor 108 may be used to provide a procedure-specific workflow to a user to complete an intraluminal imaging procedure. This workflow may include performing a pre-stent plan to determine the state of a lumen and potential for a stent, as well as a post-stent inspection to determine the status of a stent that has been positioned in a lumen. The workflow may be presented to a user as any of the displays or visualizations shown in FIGS. 5-7.

The external imaging system 132 can be configured to obtain x-ray, radiographic, angiographic/venographic (e.g., with contrast), and/or fluoroscopic (e.g., without contrast) images of the body of a patient (including the vessel 120). External imaging system 132 may also be configured to obtain computed tomography images of the body of patient (including the vessel 120). The external imaging system 132 may include an external ultrasound probe configured to obtain ultrasound images of the body of the patient (including the vessel 120) while positioned outside the body. In some embodiments, the system 100 includes other imaging modality systems (e.g., MRI) to obtain images of the body of the patient (including the vessel 120). The processing system 106 can utilize the images of the body of the patient in conjunction with the intraluminal images obtained by the intraluminal device 102.

Figure 2:
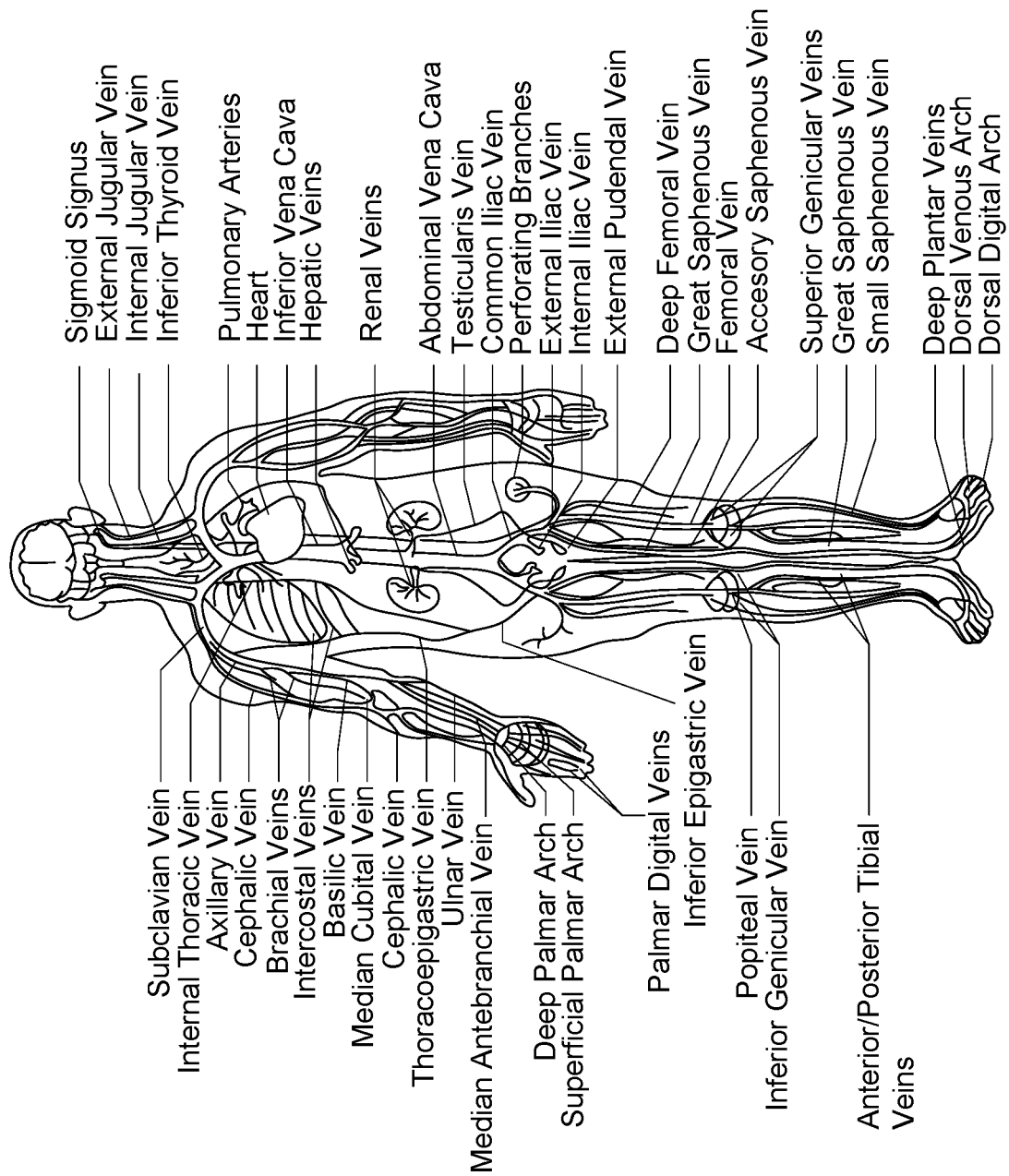
FIG. 2 illustrates blood vessels (e.g., arteries and veins) in the human body.

FIG. 2 illustrates blood vessels (e.g., arteries and veins) in the human body. For example, veins of the human body are labeled. Aspects of the present disclosure can be related to peripheral vasculature, e.g., veins in the torso or legs.

Occlusions can occur in arteries or veins. An occlusion can be generally representative of any blockage or other structural arrangement that results in a restriction to the flow of fluid through the lumen (e.g., an artery or a vein), for example, in a manner that is deleterious to the health of the patient. For example, the occlusion narrows the lumen such that the cross-sectional area of the lumen and/or the available space for fluid to flow through the lumen is decreased. Where the anatomy is a blood vessel, the occlusion may be a result of narrowing due to compression (e.g., from external vessels), plaque buildup, including without limitation plaque components such as fibrous, fibro-lipidic (fibro fatty), necrotic core, calcified (dense calcium), blood, and/or different stages of thrombus (acute, sub-acute, chronic, etc.). In some instances, the occlusion can be referenced as thrombus, a stenosis, and/or a lesion. Generally, the composition of the occlusion will depend on the type of anatomy being evaluated. Healthier portions of the anatomy may have a uniform or symmetrical profile (e.g., a cylindrical profile with a circular cross-sectional profile). The occlusion may not have a uniform or symmetrical profile. Accordingly, diseased or compressed portions of the anatomy, with the occlusion, will have a non-symmetric and/or otherwise irregular profile. The anatomy can have one occlusion or multiple occlusions.

Build-up of occlusion (e.g., thrombus, deep vein thrombosis or DVT, chronic total occlusion or CTO, etc.) is one way in which the cross-sectional area of the vein in the peripheral vasculature (e.g., torso, abdomen, groin, leg) may be reduced. Other anatomy that contacts the vein can also reduce its cross-sectional area, thereby restricting blood flow therethrough. For example, arteries or ligaments in the torso, abdomen, groin, or leg can press against a vein, which changes the shape of the vein and reduces its cross-sectional area. Such reductions in cross-sectional area resulting from contact with other anatomy can be referenced as compression, in that the walls of the vein are compressed as a result of the contact with the artery or ligament.

Human blood vessels are branched structures that are generally larger (e.g., having greater diameter or cross-sectional area) in a more proximal location and smaller (e.g., having smaller diameter or cross-sectional area) in a more distal location, and frequent bifurcations along the length of a given vessel. In the vicinity of a bifurcation or side branch, it may be a matter of opinion whether the vessel comprises two adjacent vessels, each with its own measurements (e.g., diameter or cross-sectional area), or a single vessel (perhaps with a complex shape) having only a single set of measurements.

Figure 3:
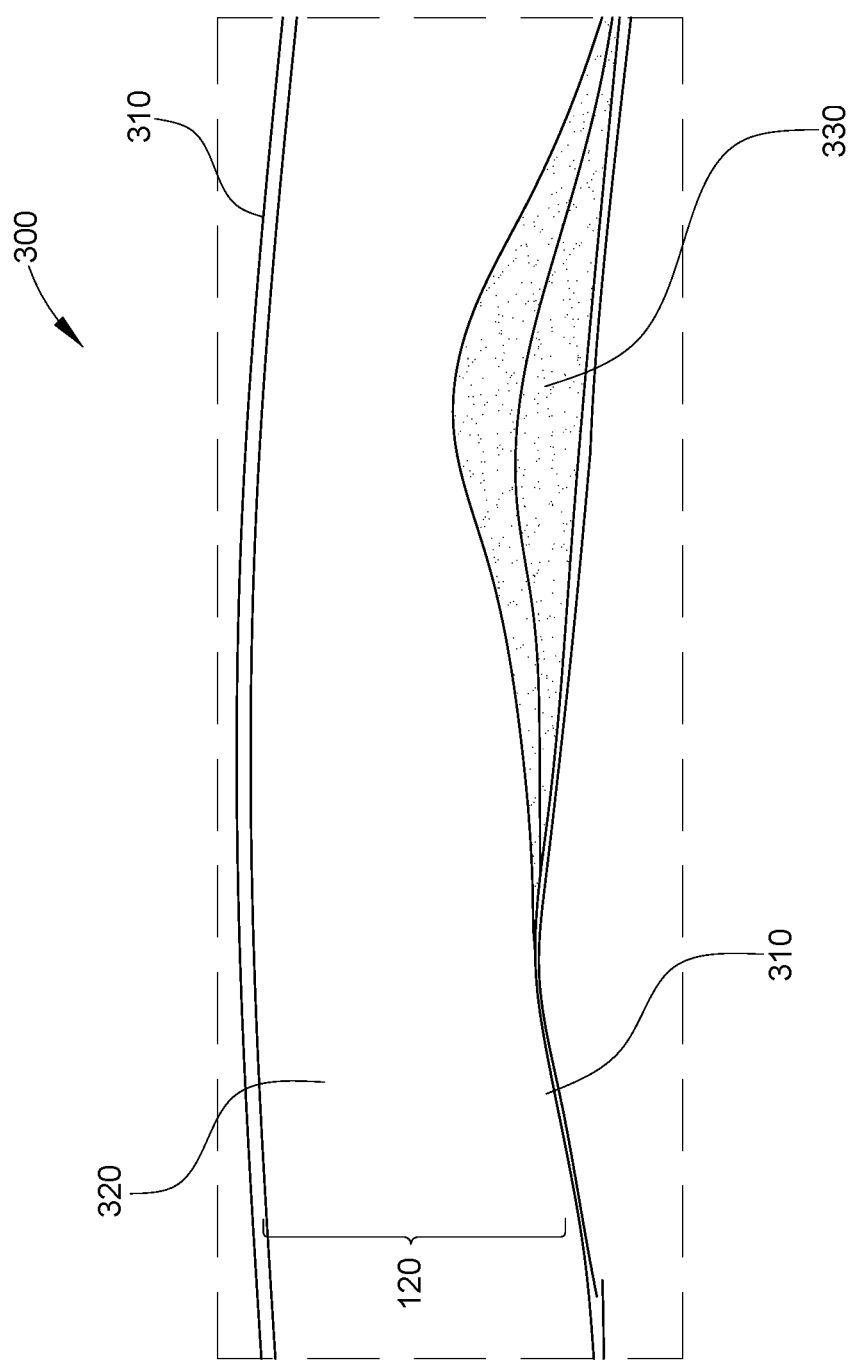
FIG. 3 illustrates a blood vessel incorporating a compression.

FIG. 3 illustrates a blood vessel 300 incorporating a compression or thrombus 330. The compression or thrombus 330 may occurs outside the vessel walls 310, within the vessel lumen 120, or as an enlargement or thickening of the vessel walls 310, and may restrict the flow of blood 320 within the lumen 120. A compression may be caused by other anatomical structures outside the blood vessel 300, including but not limited to a tendon, ligament, or neighboring lumen.

Figure 4:
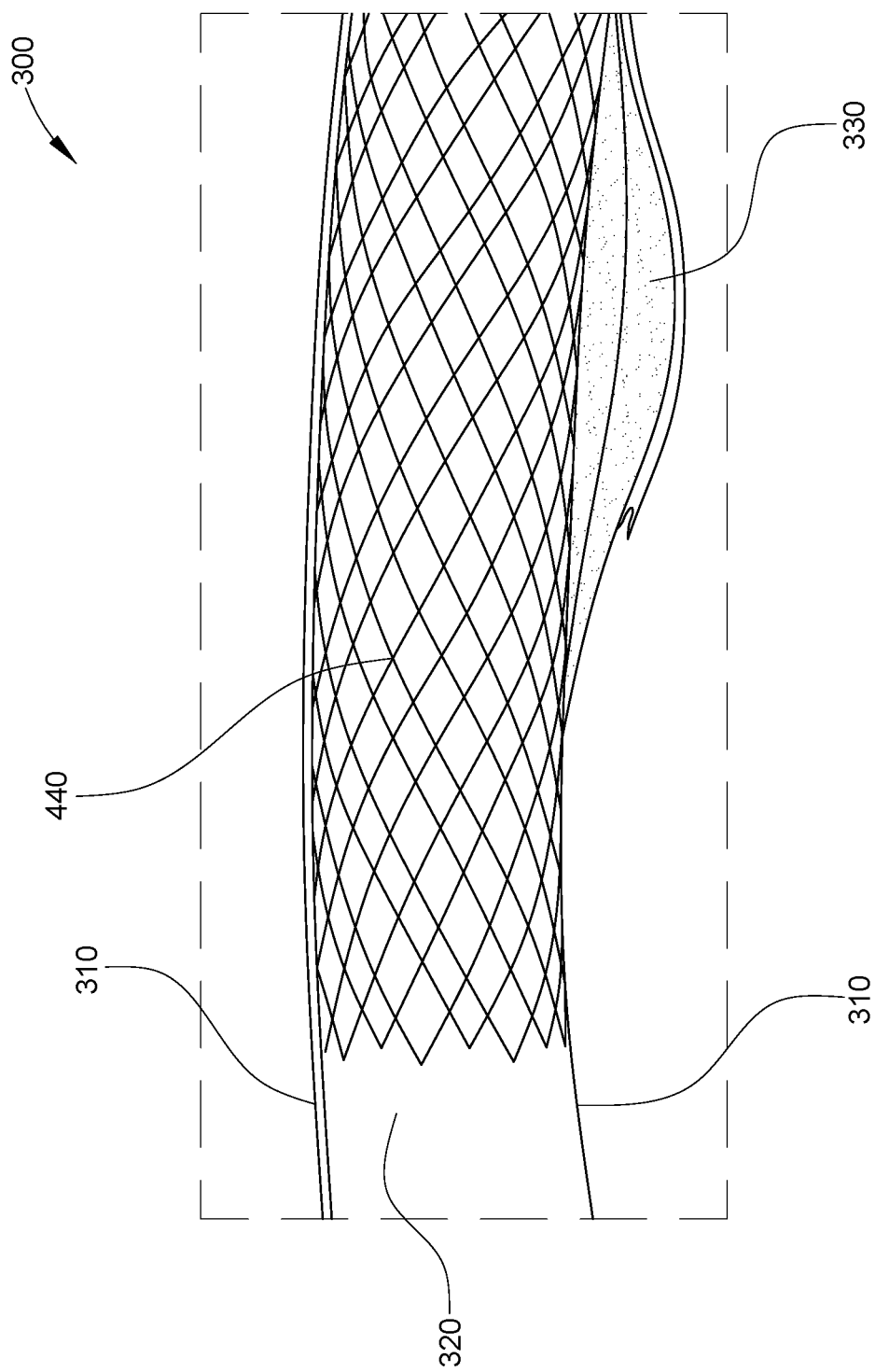
FIG. 4 illustrates a blood vessel incorporating a compression and with a stent expanded inside it to restore flow.

FIG. 4 illustrates a blood vessel 300 incorporating a compression 330 and with a stent 440 expanded inside it to restore flow. The stent 440 displaces and arrests the compression 330, pushing the vessel walls 310 outward, thus increasing the cross-sectional area of the vessel lumen and reducing the flow restriction for the blood 320. Other treatment options for alleviating an occlusion may include but are not limited to thrombectomy, ablation, angioplasty, and pharmaceuticals. However, in a large majority of cases it may be highly desirable to obtain accurate and timely intravascular images of the affected area, along with accurate and detailed knowledge of the location, orientation, length, volume, diameter, and cross-sectional area of the affected area prior to, during, or after treatment. Such information relies on accurate assessment of the vessel borders, e.g., the vessel lumen boundary and/or the outer boundary of the vessel wall 310.

Figure 5:
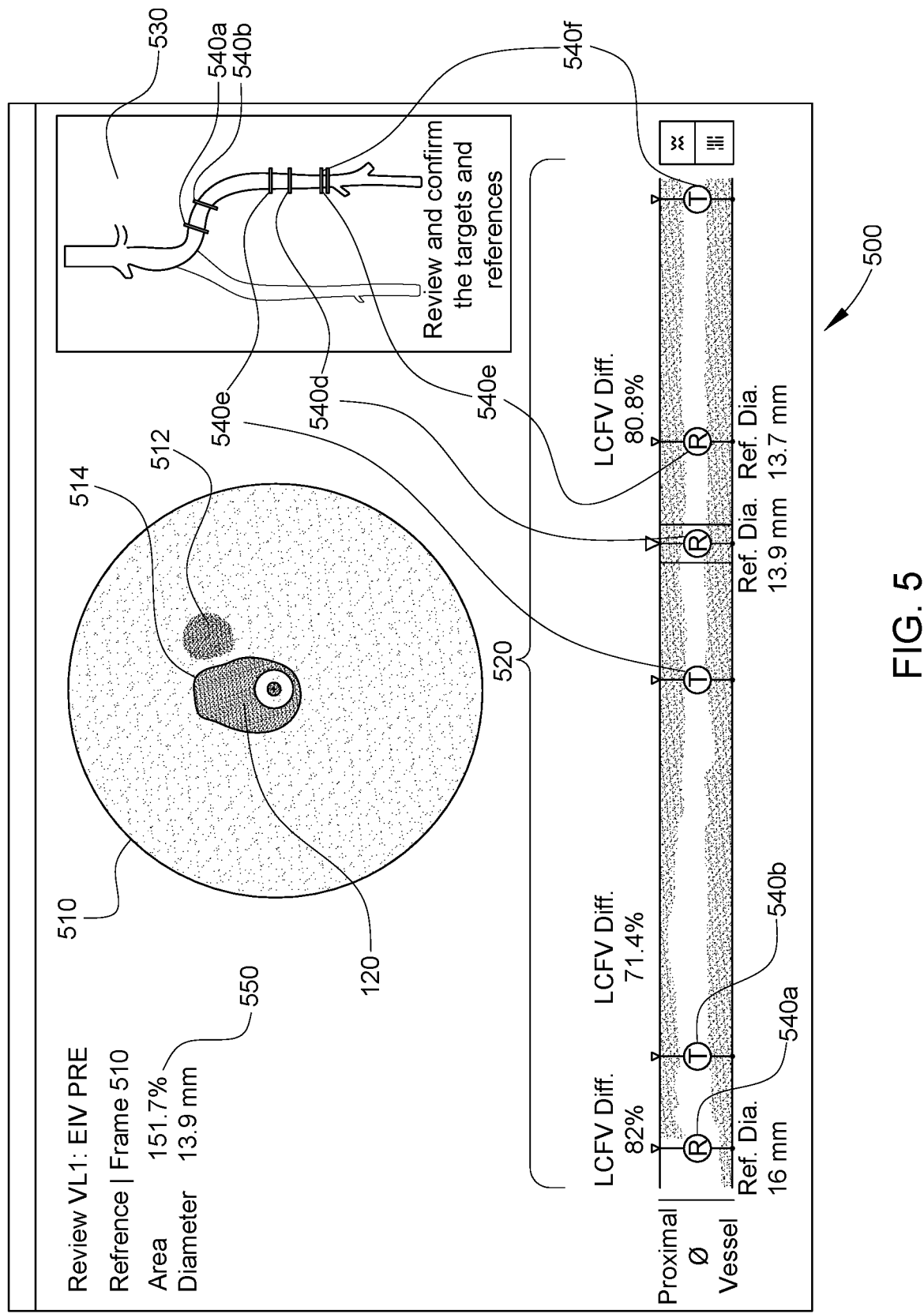
FIG. 5 illustrates an example intraluminal imaging display screen in accordance with at least one embodiment of the present disclosure.

FIG. 5 illustrates an example intraluminal imaging display screen 500 in accordance with at least one embodiment of the present disclosure. In this example, the screen display 500 includes a current tomographic IVUS image 510 from a series of successive tomographic images of a vessel. Visible is the vessel lumen 120 along with a side branch 512, representing s second lumen branching off from the lumen 120. An automatically computed vessel lumen border or boundary 514 has been overlaid on top of the image. The automatically computed vessel lumen boundary may be used for example in computing additional variables such as lumen diameter or lumen cross-sectional area, which may be useful in making clinical decisions such as stent sizing.

Examples of automatic border or boundary detection, image processing, image analysis, and/or pattern recognition include U.S. Pat. No. 6,200,268 entitled "VASCULAR PLAQUE CHARACTERIZATION" issued Mar. 13, 2001 with D. Geoffrey Vince, Barry D. Kuban and Anuja Nair as inventors, U.S. Pat. No. 6,381,350 entitled "INTRAVASCULAR ULTRASONIC ANALYSIS USING ACTIVE CONTOUR METHOD AND SYSTEM" issued Apr. 30, 2002 with Jon D. Klingensmith, D. Geoffrey Vince and Raj Shekhar as inventors, U.S. Pat. No. 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, U.S. Pat. No. 7,175,597 entitled "NON-INVASIVE TISSUE CHARACTERIZATION SYSTEM AND METHOD" issued Feb. 13, 2007 with D. Geoffrey Vince, Anuja Nair and Jon D. Klingensmith as inventors, U.S. Pat. No. 7,215,802 entitled "SYSTEM AND METHOD FOR VASCULAR BORDER DETECTION" issued May 8, 2007 with Jon D. Klingensmith, Anuja Nair, Barry D. Kuban and D. Geoffrey Vince as inventors, U.S. Pat. No. 7,359,554 entitled "SYSTEM AND METHOD FOR IDENTIFYING A VASCULAR BORDER" issued Apr. 15, 2008 with Jon D. Klingensmith, D. Geoffrey Vince, Anuja Nair and Barry D. Kuban as inventors and U.S. Pat. No. 7,463,759 entitled "SYSTEM AND METHOD FOR VASCULAR BORDER DETECTION" issued Dec. 9, 2008 with Jon D. Klingensmith, Anuja Nair, Barry D. Kuban and D. Geoffrey Vince, as inventors, the teachings of which are hereby incorporated by reference herein in their entirety.

Also visible in FIG. 5 is a graphical roadmap 530, along with an Image Longitudinal Display (ILD) 520 of the vessel, comprising stacked cross-sections of the series of successive tomographic images, forming a longitudinal cross-sectional image of the vessel. Additionally. Bookmarks 540a, 540b, 540c, 540d, 540e, and 540f, are associated with both the graphical roadmap 530 and the ILD 520. In this example, bookmark 540d is also associated with the current IVUS image 510, as is a label 550 that contains information about the location and nature of the IVUS image 510.

Figure 6:
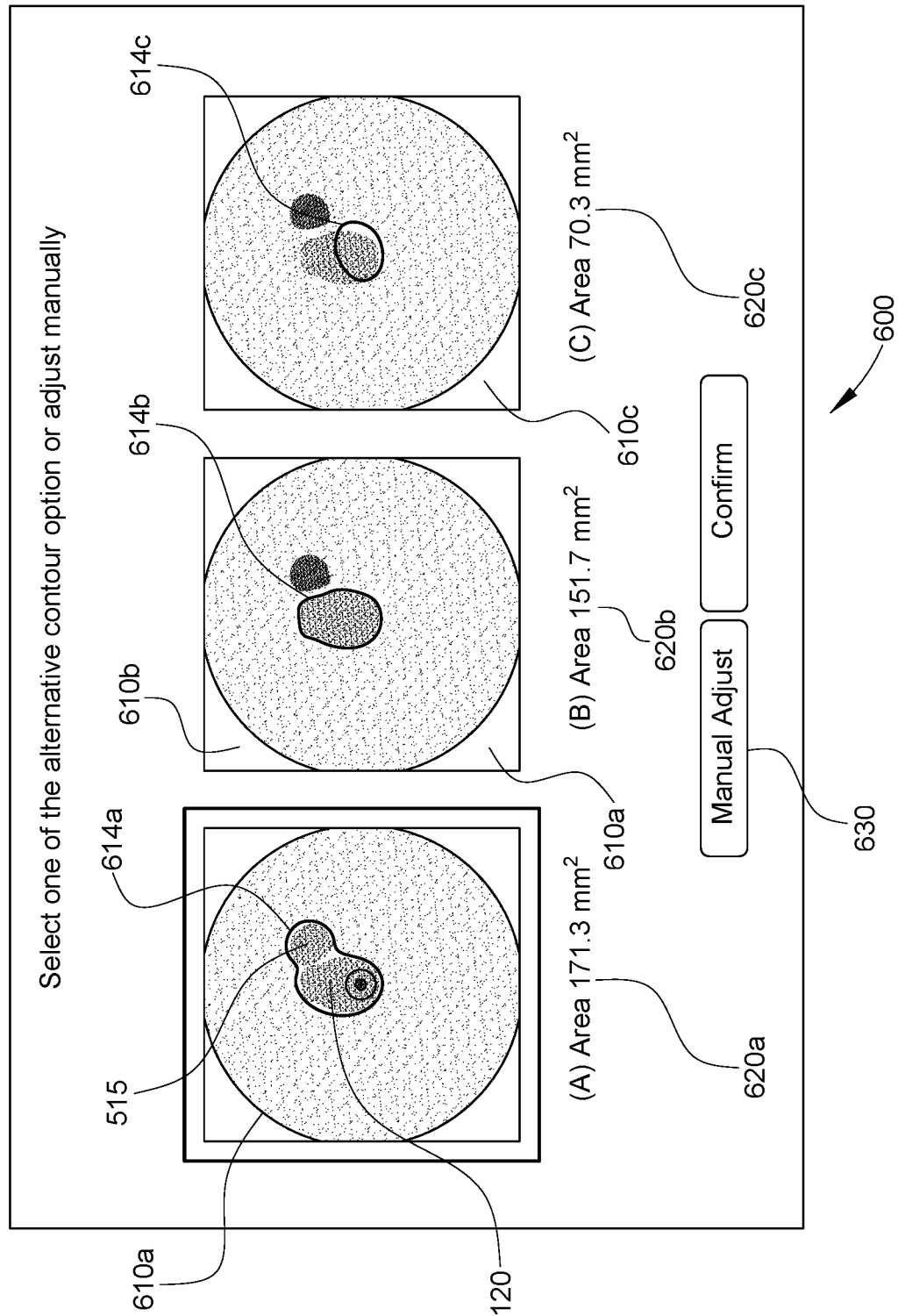
FIG. 6 shows an example contour selection screen display, in accordance with at least one embodiment of the present disclosure.

FIG. 6 shows an example contour selection screen display 600, in accordance with at least one embodiment of the present disclosure. In this example, the contour selection screen display screen display 600 includes three different instances 610a, 610b, and 610c of the same tomographic image (e.g., a lateral or radial cross sectional image substantially perpendicular to the longitudinal axis of the vessel). Visible in each instance 610a, 610b, and 610c is the vessel lumen 120 and the side branch 515. Where side branches occur in a tomographic image (e.g., an IVUS image), determining the lumen boundary of the vessel becomes difficult, as for any given frame it may be a matter of individual clinical preference whether the side branch is considered part of the main vessel or not. Other sources of ambiguity in the lumen boundary may include, but are not limited to, complex (e.g., concave or bean-shaped) vessel geometries, occlusions, compressions, stenoses, and stents, including suboptimally placed or suboptimally expanded stents.

In this example, instead of a single automatically computed lumen boundary as seen for example in FIG. 5, the contour selection screen display 600 offers three different choices 614a, 614b, and 614c of computed lumen boundary, each with its own associated lumen measurement or other numerical value 620a, 620b, and 620c (e.g., a lumen diameter in mm or a lumen cross-sectional area in $mm^2$). In an example, the choices represent the boundary detection algorithm's three likeliest lumen boundary contours. The algorithm may identify other possible lumen boundary contours, but not show them if they are not one of the three most probable. In other embodiments, the number of choices may be a number other than three, such as but not limited to two choices, four choices, or five choices. In an example, a clinician or other user may select one of the suggested lumen boundaries 614a, 614b, or 614c with a user interface (e.g., mouse, trackball, touch screen, or keyboard), either by selecting the associated tomographic image or by selecting an alphanumeric symbol associated with the image (e.g., A, B, C, etc.), or by other similar means.

In some embodiments, the display and the user interface may be the same device. In an exemplary embodiment, the multiple instances of the same IVUS image, with the corresponding candidate boundaries and measurement, are displayed on a touch screen display. The user input can be a touch input on the touch screen display selecting one of the candidates. In other embodiments, the display and user interface can be different devices that are either directly/indirectly coupled other another or separate/spaced from other another.

In some embodiments, the border detection algorithm employs a machine learning network such as a deep learning, deep structured learning, or deep hierarchical learning network (e.g., a learning artificial neuron network (ANN) with multiple layers between the input and output layers), trained on sets of comparable IVUS image data using human-identified lumen borders. Examples of deep learning networks include but are not limited to a convolutional neural network (CNN, e.g., a fully connected network), deep belief network (e.g., a network with connections between the layers but not between units within each layer), or deep Boltzmann machine. A border detection algorithm may yield multiple candidate border contours, each with a probability, confidence level, or confidence interval associated therewith.

The processor circuit will generate and output different border candidates based on the statistical measure (probability, confidence interval, confidence level). That is, the processor circuit will generate and output a set of border candidates for a given value of the statistical measure, and output and generate a different set of border candidates for a different value of the statistical measure. In various instances, the two sets of border candidates can be the same (e.g., all same candidates), completely different (e.g., none of the same candidates), or partially different (e.g., some same candidates, some different candidates). This selection of the statistical measure may be performed for example through a user input.

In some embodiments, the minimum confidence interval for a candidate lumen boundary is a user-editable parameter, although default values may also be supplied by the system. In some embodiments, the vessel border selection system may show fewer choices if one or more of the possible lumen boundary contours does not exceed the minimum confidence interval, and more choices if several possible lumen boundary contours exceed the minimum confidence interval. Thus, for regions where the vessel lumen has a simple, nearly circular cross section, the algorithm may identify fewer possible lumen boundaries 614, whereas for regions where the vessel lumen has a complex, concave (e.g., bean shaped), bifurcated or otherwise ambiguous cross section, the algorithm may identify more possible lumen boundaries 614 from which a clinician or other user may select.

Also visible is an Manual Adjust button 630 which, in some embodiments, enables the clinician or other user to adjust the individual points comprising the selected lumen boundary 614. In some embodiments, a user may enter a manual adjust mode automatically, and have the option of either editing or not editing the vessel border contour. In other embodiments, border editing may be done directly on the displayed border contour options, e.g., by clicking and dragging on portions of the vessel border contour, or by activating and interacting with a pop-up window with the selected option. Other means of manual adjustment of border contours are also contemplated.

In some embodiments, the border contour can be a natural contour of the body, such as the lumen border, the vessel border, the intima-media border, the media-adventitia border, etc. In some embodiments, the border contour can be a contour of a medical device within the vessel of the patient, such as a stent border.

Some embodiments of the present disclosure can include features described in U.S. Provisional App. No. 62/642,847, filed Mar. 14, 2018, which is hereby incorporated by reference in its entirety as though fully set forth herein.

Figure 7:
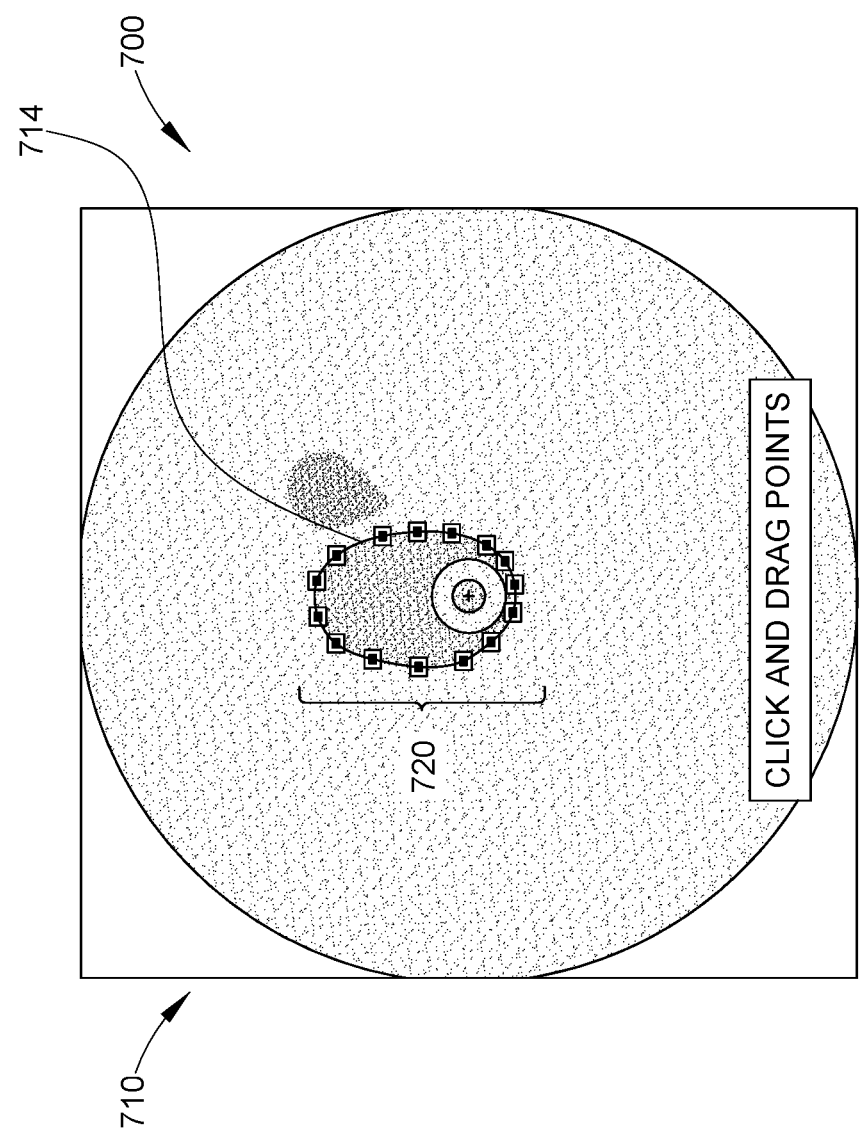
FIG. 7 shows an example lumen border contour editing screen display, in accordance with at least one embodiment of the present disclosure.

FIG. 7 shows an example lumen border contour editing screen display 700, in accordance with at least one embodiment of the present disclosure. In some embodiments, if the clinician or other user selects the Manual Adjust button 630 from FIG. 6, or a similar control, the system shows the selected tomographic image 710 along with the selected lumen boundary 714. However, the system also shows a plurality of points 720 that define the lumen boundary 714. By selecting and moving these points (e.g., using a touchscreen, keyboard, mouse, or trackball), the clinician or other user is able to alter the lumen boundary 714. This option may be used, for example, if the clinician or other user is dissatisfied with all of the choices offered by the lumen border detection algorithm. In such an instance, the clinician or other user could, for example, select the closest match from the available choices, and then hand edit one or more points until the lumen boundary 714 matches the user's expectation. In some embodiments, the edited lumen boundary 714 is fed back into the training of a border detection neural network or other learning algorithm.

It is noted that manual adjustment of a vessel border contour may be performed in any suitable manner, not just by moving discrete points. For example, the display could show just be the identified contour itself, and the user may touch and drag the contour itself to change the shape. In some instances, the user may be able to draw all or a portion of the contour via touch input. An editing screen, editing window, or editing option for the selected border contour could be entered using one or more inputs. If the user is editing directly on the screen with the multiple instances of the same IVUS frame, only one input may be needed. If a user selected a button or other input to enter manual edit mode, an additional input may be required to actually edit the border.

Figure 8:
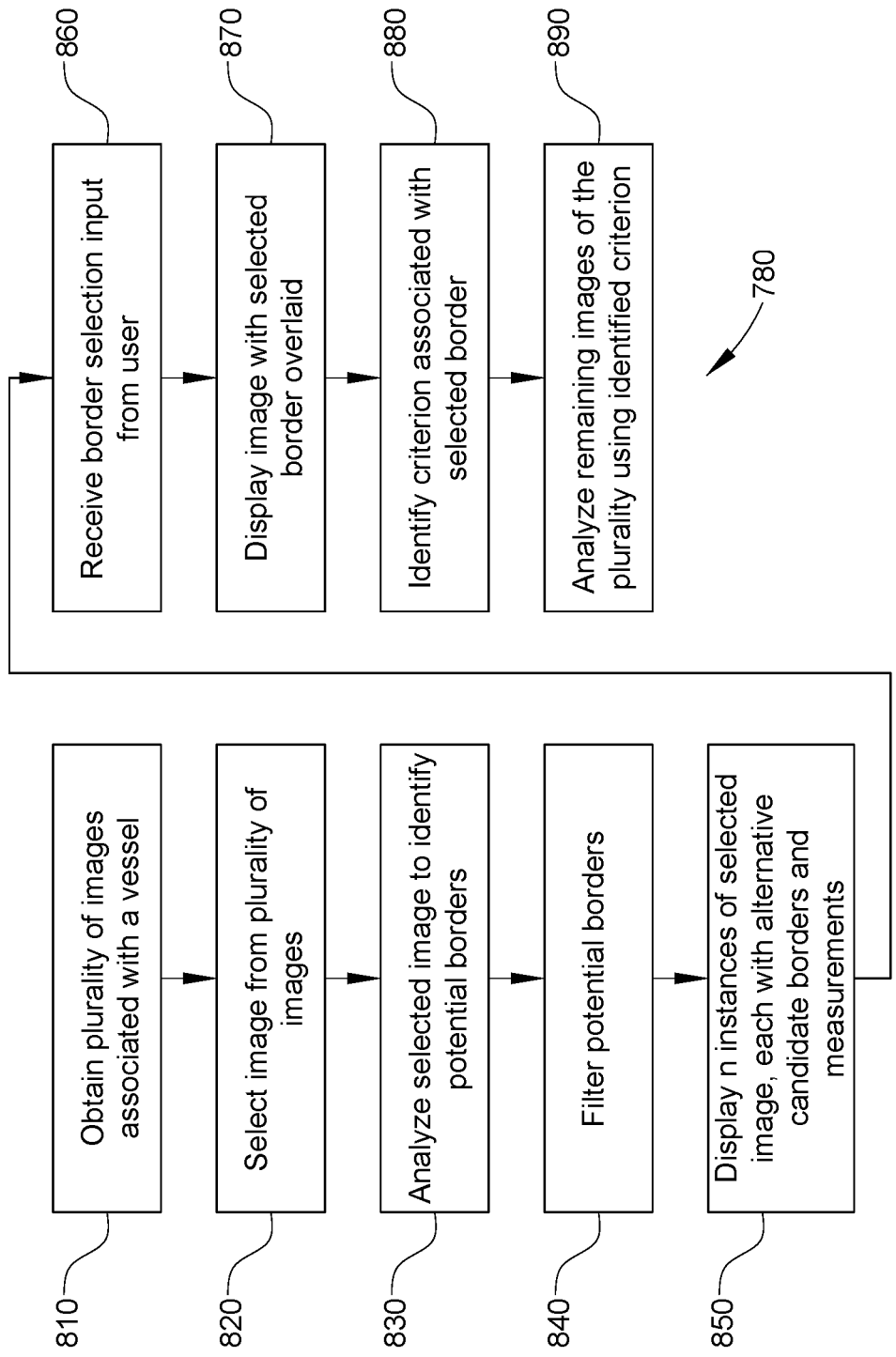
FIG. 8 is a flow diagram illustrating a method for blood vessel identification, in accordance with at least one embodiment of the present disclosure.

FIG. 8 is a flow diagram illustrating a method 800 for blood vessel identification, in accordance with at least one embodiment of the present disclosure. In some embodiments, one or more of the steps of the method 800 may be carried out by an intraluminal medical imaging system.

In step 810, an intraluminal medical imaging system obtains a plurality of images associated with a blood vessel. In some embodiments, each of the plurality of images may be obtained at different locations of the blood vessel, or at different times or orientations within the blood vessel. In some embodiments, the plurality of images may be obtained sequentially along a length of the blood vessel. In some embodiments, the plurality of images obtained along the length of the blood vessel may be used to create a two-dimensional and/or three-dimensional representation of the blood vessel.

In step 820, the system selects one of the plurality of images of the blood vessel. In some embodiments, the selected image may be the first or last image obtained sequentially along a length of the blood vessel, or may be an intermediate image obtained along the length of the blood vessel. The image may for example be a target frame within a region of interest (e.g., the frame representing the maximum occlusion or minimum lumen cross-sectional area within a diseased or compressed portion of a vessel), or a reference frame (e.g., healthy tissue proximal or distal to a diseased or compressed portion of a vessel). In some embodiments, the image selection may be done manually by a clinician or other user through a user interface. In other embodiments, the image selection is made automatically by an algorithm (e.g., an algorithm for selecting target and reference frames from an image data set).

In step 830, the vessel border selection system analyzes the selected image to identify one or more potential borders in the image, such as a circumference of the blood vessel in the image. In some embodiments, the identified potential borders may represent a lumen border, a blood vessel border, an inner wall of the blood vessel, and/or an outer wall of the blood vessel. The analysis may be performed by one or more components of the medical imaging system, such as a processing unit, a user display, or the medical imaging device. The borders can be identified using any suitable anatomical border detection algorithm. Such automated algorithms may be built on classical techniques or may incorporate machine learning or deep learning techniques or other types of artificial intelligence, or combinations thereof. With deep learning or classical algorithms there are means to determine the probability of the features an algorithm is built to detect. Consequently, each automatically identified border may also have an associated probability or confidence interval computed by the algorithm.

In step 840, the vessel border selection system compares the potential borders to one another and/or to a threshold value, and filters them accordingly. For example, in some embodiments, one or more diameter or cross-sectional area values of the potential borders may be compared to one another, or to a threshold value, and potential borders may be filtered out based on comparison. For example, vessel border contours with a cross-sectional area below a user-definable minimum threshold value or above a user-definable maximum threshold value may be filtered out by the algorithm. Further, the algorithm may filter out identified lumen borders with a probability or confidence interval below a threshold value. Once unwanted or unsuitable candidate borders have been filtered out, the medical imaging system may optionally identify one or more alternative candidate borders from the potential borders.

In step 850, the medical imaging system outputs two or more instances of the selected image of the blood vessel to the user display, each with a candidate border contour superimposed on it that has been computed in step 840. As described above, in some embodiments, the one or more alternative candidate borders may comprise alternative representations of the same anatomical feature or border, such as an inner wall of the blood vessel at a specific point along a path of the blood vessel. In some embodiments, the imaging system may pre-select select one of the alternative candidate borders as the primary candidate border, so that a clinician or other user need only confirm the selection in order to accept it. The candidate borders may be ranked based, for example, on their relative probabilities or confidence intervals, such that the most probable selection appears first (e.g., on the top or left), and the least probable appears last (e.g., on the right or bottom), although other arrangements may be used instead or in addition. Each candidate border has a vessel measurement or other numerical value (e.g., a diameter or cross-sectional area) associated with it, which is also displayed, such that the measurements of each border candidate can be used by a clinician or other user to determine which candidate border to select, and optionally whether to manually edit its points before finally selecting it.

In step 860, the system receives a border selection input from a user. The border selection input may be transmitted to the system via a user interface. In some embodiments, the user interface may comprise a touch screen device, a mouse, a keyboard, a joystick, and/or any other suitable component configured to receive a user input associated with a candidate border contour. The border selection input may include an instruction to select one of the one or more alternative candidate borders. In some embodiments, the system in step 850 may first display only the primary or a "best choice" candidate border. The border selection input can then include an instruction to proceed with the primary or best border identified by the system if the clinician or other user is satisfied with the primary candidate border. In other embodiments, if a user is satisfied with the primary candidate border displayed, no border selection input is required. For example, the primary candidate border can be accepted by default. In that regard, the system may continue to display the primary candidate border overlaid on the image of the blood vessel, and may proceed to other steps (e.g., further image processing, calculations based on the primary candidate border dimensions, etc.) In other embodiments, the border selection input may include an instruction to select one of the simultaneously displayed candidate borders. In embodiments in which the primary candidate border is accepted by default, a user can provide a border selection input such that the system outputs one or more alternative candidate borders when the user is not satisfied with the primary candidate border. A further border selection input can be provided by the user to select one of the alternative candidate borders.

In some embodiments, the border selection input may include an instruction to reject one or more of the one or more alternative candidate borders. In some embodiments, the border selection input may include an instruction to modify one of the one or more alternative candidate borders.

In step 870, after a candidate border contour has been selected with a border selection input, the system can display the image of the blood vessel with the selected candidate border overlaid on the image.

In step 880, the system may identify a criterion associated with the selected border. The criterion may comprise a diameter or cross-sectional area value, or another value associated with the selected border's position, orientation, size, or shape on the image. In some embodiments, the image may identify several criteria associated with the selected image. In some embodiments, the criterion or criteria may comprise coefficients of a formula used to identify contour lines in an image. In other embodiments, the criterion or criteria can comprise one or more locations on the image corresponding to an area or region on the image wherein a desired border is likely to be found.

In step 890, the system can propagate the identified criterion and/or the identified border to the remaining images of the plurality as starting points to identify or detect one or more derived borders in each of the plurality of images. By using the identified criterion or border as a starting point, the system may be more likely to consistently identify or derive a border in the vessel across images. By propagating the identified criterion or border to each of the plurality of images, the clinician or other user may not need to revisit each of the plurality of images to ensure that a satisfactory border has been identified.

It should be noted that identified borders associated with the lumen can include the lumen border, the vessel border, intima/media border, media/adventitia border, and/or or any other border, contour, and/or segmentation of any structure in the intravascular and/or intraluminal image. For example, the lumen border can be the border between blood and vessel tissue. For example, the vessel border can be the border between the vessel tissue and surrounding tissue. The border can an automatically drawn contour around an identified structure, which could be the lumen, vessel, chamber, valve, thrombus, calcium, neighboring artery or vein (blood vessel), stent contour, or other structure.

In some embodiments, each of the potential borders identified by the medical imaging system can be a candidate border to be displayed to a user display such that no filtering step is necessary. In some embodiments, a method may comprise selecting multiple borders from a plurality of candidate borders to be displayed to the user display. For example, in some embodiments, a method may comprise selecting an outer border of a vessel wall and an inner border of the same vessel wall to display both the outer border and inner border on the user display.

Figure 9:
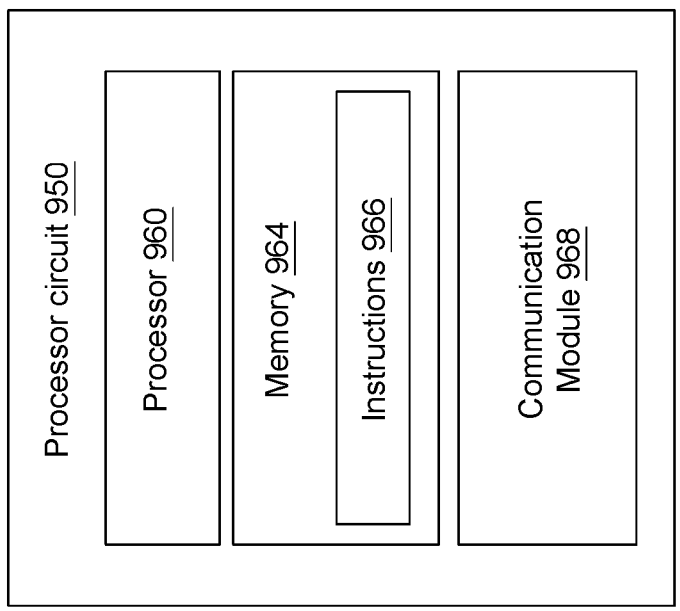
FIG. 9 is a schematic diagram of a processor circuit, according to embodiments of the present disclosure.

FIG. 9 is a schematic diagram of a processor circuit 950, according to embodiments of the present disclosure. The processor circuit 950 may be implemented in the ultrasound imaging system 100, or other devices or workstations (e.g., third-party workstations, network routers, etc.), or on a cloud processor or other remote processing unit, as necessary to implement the method. As shown, the processor circuit 950 may include a processor 960, a memory 964, and a communication module 968. These elements may be in direct or indirect communication with each other, for example via one or more buses.

The processor 960 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 960 may also comprise another hardware device, a firmware device, or any combination thereof configured to perform the operations described herein. The processor 960 may also be implemented as a combination of computing devices, e.g., a combination of a DSP and a microprocessor, a plurality of microprocessors, one or more microprocessors in conjunction with a DSP core, or any other such configuration.

The memory 964 may include a cache memory (e.g., a cache memory of the processor 960), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 964 includes a non-transitory computer-readable medium. The memory 964 may store instructions 966. The instructions 966 may include instructions that, when executed by the processor 960, cause the processor 960 to perform the operations described herein. Instructions 966 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The communication module 968 can include any electronic circuitry and/or logic circuitry to facilitate direct or indirect communication of data between the processor circuit 950, and other processors or devices. In that regard, the communication module 968 can be an input/output (I/O) device. In some instances, the communication module 968 facilitates direct or indirect communication between various elements of the processor circuit 950 and/or the ultrasound imaging system 100. The communication module 968 may communicate within the processor circuit 950 through numerous methods or protocols. Serial communication protocols may include but are not limited to US SPI, I$^2$C, RS-232, RS-485, CAN, Ethernet, ARINC 429, MODBUS, MIL-STD-1553, or any other suitable method or protocol. Parallel protocols include but are not limited to ISA, ATA, SCSI, PCI, IEEE-488, IEEE-1284, and other suitable protocols. Where appropriate, serial and parallel communications may be bridged by a UART, USART, or other appropriate subsystem.

External communication (including but not limited to software updates, firmware updates, or readings from the ultrasound device) may be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media such as a USB flash drive or memory stick.

A number of variations are possible on the examples and embodiments described above. For example, the vessel border selection system may be employed in anatomical systems within the body other than those described, or may be employed to image other disease types, object types, or procedure types than those described. The technology described herein may be applied to imaging sensors of diverse types, whether currently in existence or hereinafter developed. The system may be employed with IVUS for coronary arterial and peripheral use in arterial or venous imaging, such as IVUS console software. Alternatively or in addition, the system may be employed with X-ray, angiogram, and venogram applications that enable automated measurements and hence may require editing of automatically identified border contours. The system may be applied to any imaging modality with automated feature detection or measurements enabled, but with allowed editing of those findings, in order to streamline the editing process.

Accordingly, the logical operations making up the embodiments of the technology described herein are referred to variously as operations, steps, objects, elements, components, or modules. Furthermore, it should be understood that these may occur or be performed in any order, unless explicitly claimed otherwise or a specific order is inherently necessitated by the claim language. All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the vessel border selection system. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." Unless otherwise noted in the claims, stated values shall be interpreted as illustrative only and shall not be taken to be limiting.

The above specification, examples and data provide a complete description of the structure and use of exemplary embodiments of the vessel border selection system as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter. Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. An intraluminal ultrasound imaging system, comprising:
   a processor circuit configured for communication with an intraluminal ultrasound imaging catheter, wherein the processor circuit is configured to:
      receive a plurality of intraluminal ultrasound images obtained by the intraluminal ultrasound imaging catheter during movement of the intraluminal ultrasound imaging catheter within a body lumen of a patient;
      select an image from among the plurality of intraluminal ultrasound images;
      generate a first contour option and a second contour option associated with the body lumen within the selected image, wherein the first contour option and the second contour option comprise alternative representations of a same anatomical border; and output, to a display in communication with the processor circuit, a screen display comprising a first copy of the selected image overlaid with the first contour option and a second copy of the selected image overlaid with the second contour option, wherein the first copy of the selected image is located in a first portion of the screen display and the second copy of the selected image is located in a second portion of the screen display such that the first copy of the selected image and the second copy of the selected image are displayed simultaneously.

2. The system of claim 1, wherein the processor circuit is configured to:

receive, from a user interface in communication with the processor circuit, a first user input selecting one of the first contour option or the second contour option; and output, to the display, the selected image overlaid with the selected contour option.

3. The system of claim 2, wherein the processor circuit is further configured to:

generate a derived contour associated with the body lumen for at least one additional image from the plurality of intraluminal ultrasound images by propagating the selected contour option of the selected image to the at least one additional image.

4. The system of claim 1, wherein the processor circuit is further configured to:

generate a geometric measurement for each of the first contour option and the second contour option; and output, to the display, the geometric measurement for each of the first contour option and the second contour option.

5. The system of claim 4, wherein the geometric measurement comprises at least one of a lumen diameter, a vessel wall outer diameter, a lumen cross-sectional area, or a vessel cross-sectional area.

6. The system of claim 2, wherein the processor circuit is further configured to:

receive, from the user interface, a second user input to edit the selected contour option;

calculate a geometric measurement based on the edited contour option; and output, to the display, the selected image overlaid with the edited contour option and the calculated geometric measurement.

7. The system of claim 1, wherein the processor circuit is configured to generate the first contour option and the second contour option based on a first value of a statistical measure, and wherein the processor circuit is configured to generate a third contour option based on a second value of the statistical measure.

8. The system of claim 7, wherein the processor circuit is configured to receive a second input, from the user interface, to change the statistical measure from the first value to the second value.

9. The system of claim 1, wherein the processor circuit is configured to generate the first contour option and the second contour option based on a machine learning algorithm.

10. The system of claim 1, further comprising:
the intraluminal ultrasound imaging catheter.

11. The system of claim 1, further comprising:
the display; and the user interface, wherein the user interface comprises a touch screen of the display.

12. An intraluminal ultrasound imaging method, comprising:

receiving, at a processor circuit in communication with an intraluminal ultrasound imaging catheter, a plurality of intraluminal ultrasound images obtained by the intraluminal ultrasound imaging catheter during movement of the intraluminal ultrasound imaging catheter within a body lumen of a patient;

selecting, using the processor circuit, an image from among the plurality of intraluminal ultrasound images;

generating, using the processor circuit, a first contour option and a second contour option associated with the body lumen within the selected image, wherein the first contour option and the second contour option comprise alternative representations of a same anatomical border;

outputting, to a display in communication with the processor circuit, a screen display comprising a first copy of the selected image overlaid with the first contour option and a second copy of the selected image overlaid with the second contour option, wherein the first copy of the selected image is located in a first portion of the screen display and the second copy of the selected image is located in a second portion of the screen display such that the first copy of the selected image and the second copy of the selected image are displayed simultaneously.

13. The method of claim 12, further comprising:

receiving, from a user interface in communication with the processor circuit, a first user input selecting one of the first contour option or the second contour option; and outputting to the display, using the processor circuit, the selected image overlaid with the selected contour option.

14. The method of claim 13, further comprising:

generating a derived contour associated with the body lumen for at least one additional image from the plurality of intraluminal ultrasound images by propagating the selected contour option of the selected image to the at least one additional image.

15. The method of claim 12, further comprising:

generating a geometric measurement for each of the first contour option and the second contour option; and outputting to the display the geometric measurement for each of the first contour option and the second contour option.

16. The method of claim 15, wherein the geometric measurement comprises at least one of a lumen diameter, a vessel wall outer diameter, a lumen cross-sectional area, or a vessel cross-sectional area.

17. The method of claim 13, further comprising:

receiving, from the user interface, a second user input to edit the selected contour option;

calculating a geometric measurement based on the edited contour option; and outputting, to the display, the selected image overlaid with the edited contour option and the calculated geometric measurement.

18. The method of claim 12, further comprising:

generating the first contour option and the second contour option based on a first value of a statistical measure; and generating a third contour option based on a second value of the statistical measure.

19. The method of claim 18, further comprising receiving a second input, from the user interface, to change the statistical measure from the first value to the second value.

20. The method of claim 12, wherein the first contour option and the second contour option are generated based on a machine learning algorithm.

21. An intravascular ultrasound imaging system for use in peripheral blood vessels, the system comprising:
- an intravascular ultrasound imaging catheter configured to obtain a plurality of intravascular ultrasound images during movement of the intravascular ultrasound imaging catheter within a peripheral blood vessel of a patient; and
- a processor circuit configured for communication with the intravascular ultrasound imaging catheter, wherein the processor circuit is configured to:
  - receive the plurality of intravascular ultrasound images obtained by the intravascular ultrasound imaging catheter;
  - select an image from among the plurality of intravascular ultrasound images;
  - generate a first contour option and a second contour option associated with the peripheral blood vessel within the selected image, wherein the first contour option and the second contour option comprise alternative representations of a same anatomical border; and
  - output, to a display in communication with the processor circuit, a screen display comprising a first copy of the selected image overlaid with the first contour option and a second copy of the selected image overlaid with the second contour option, wherein the first copy of the selected image is located in a first portion of the screen display and the second copy of the selected image is located in a second portion of the screen display such that the first copy of the selected image and the second copy of the selected image are displayed simultaneously.

22. The system of claim 21, wherein the processor circuit is configured to:
- receive, from a user interface in communication with the processor circuit, a first user input selecting one of the first contour option or the second contour option; and
- output, to the display, the selected image overlaid with the selected contour option.

* * * * *